US008736825B2

(12) United States Patent
Ciocan et al.

(10) Patent No.: US 8,736,825 B2
(45) Date of Patent: May 27, 2014

(54) QUANTUM EFFICIENCY MEASUREMENT SYSTEM AND METHOD OF USE

(75) Inventors: Razvan Ciocan, Auburndale, MA (US); John Donohue, Shelton, CT (US); Arkady Feldman, Stanford, CT (US); Zhuoyun Li, Worcester, MA (US)

(73) Assignee: Newport Corporation, Irvine, CA (US)

( * ) Notice: Subject to any disclaimer, the term of this patent is extended or adjusted under 35 U.S.C. 154(b) by 37 days.

(21) Appl. No.: 13/234,951

(22) Filed: Sep. 16, 2011

(65) Prior Publication Data

US 2012/0010854 A1 Jan. 12, 2012

Related U.S. Application Data

(63) Continuation of application No. PCT/US2010/035445, filed on May 19, 2010.

(60) Provisional application No. 61/216,704, filed on May 19, 2009.

(51) Int. Cl.
*G01N 21/55* (2014.01)

(52) U.S. Cl.
USPC .............................................. 356/72; 356/445

(58) Field of Classification Search
USPC ............. 136/243–246, 252; 250/200, 559.11, 250/559.15; 324/761.01, 762.02, 760.01; 356/72–73, 300–334, 445, 402–425
See application file for complete search history.

(56) References Cited

U.S. PATENT DOCUMENTS

| | | | | |
|---|---|---|---|---|
| 5,757,474 | A * | 5/1998 | Sopori et al. ..................... | 356/72 |
| 7,265,830 | B2 * | 9/2007 | Wang ............................. | 356/328 |
| 8,299,416 | B2 * | 10/2012 | Arbore et al. ............... | 250/222.2 |
| 2004/0056648 | A1 * | 3/2004 | Matsuyama .................... | 324/96 |
| 2005/0083523 | A1 * | 4/2005 | Senturia et al. ............... | 356/323 |
| 2005/0236563 | A1 * | 10/2005 | Busch et al. ............... | 250/252.1 |
| 2007/0015993 | A1 * | 1/2007 | Ciocan et al. ................. | 600/407 |

OTHER PUBLICATIONS

Botts, Steven E., Design and Performance of a SWIR HgCdTe Hybrid Module for Multispectral Linear Array/LANDSAT Applications, IEEE Transactions on Electron Devices, vol. ED-32, No. 8 (Aug. 1985), pp. 1584-1591.*

King, D.L. et al., New Methods for Measuring Performance of Monolithic Multi-Junction Solar Cells, IEEE 0-7803-5772-8/00 (2000), pp. 1197-1201.*

(Continued)

*Primary Examiner* — Kara E Geisel
(74) *Attorney, Agent, or Firm* — Brian F. Swienton; George L. Fountain; Fountain Law Group, Inc.

(57) ABSTRACT

A system for measuring a characteristic of a solar cell is disclosed and includes a light source irradiating an optical signal having a spectral range from about 100 nm to about 3000 nm, a wavelength selector configured to selectively narrow the spectral range of the optical signal, a beam splitter, a reference detector in optical communication with the beam splitter and configured to measure a characteristic of the optical signal, a specimen irradiated with the optical signal, a reflectance detector in optical communication with the specimen via the beam splitter and configured to measure an optical characteristic of the optical signal reflected by the specimen, a multiplexer in communication with at least one of the reference detector, specimen, and reflectance detector, and a processor in communication with at least one of the reference detector, specimen, and reflectance detector via the multiplexer and configured to calculate at least one characteristic of the specimen.

13 Claims, 3 Drawing Sheets

(56) References Cited

OTHER PUBLICATIONS

Field, H., UV-VIS-IR Spectral Responsivity Measurement System for Solar Cells, National Renewable Energy Laboratory, NREL/CP-520-25654 (2008), 9 pages.*

Fischer, B. et al., Scanning IQE-Measurement for Accurate Current Determination on Very Large Area Solar Cells, IEEE, 0-7803-7471-1/02 (2002), pp. 454-457.*

Willet, Dennis et al., The Effects of Sweep Rate, Voltage Bias and Light Soaking on the Measurement of CIS-Based Solar Cell Characteristics, IEEE 0-7803-1220-1/93 (1993), 495-500.*

Kim, Y. et al., High External Quantum Efficiency from Organic Bulk Heterojunction Photodetectors, Optical Society of America, 1-55752-834-9 (2007), 2 pages.*

Young, David L. et al., A New Real-Time Quantum Efficiency Measurement System, IEEE, 978-1-4244-1641-7/08 (2008), 3 pages.*

Jabbour, Ghassan E. et al, "Photovoltaics: Spectroradiometer Improves Accuracy of Photovoltaic Measurement", Jan. 1, 2008, LaserFocusWorld.

Protoflex, "Quantum Efficiency Measurement System".

Metzdorf, J. "Calibration of solar cells. 1:The differential Spectral Responsivity Method", Applied Optics 26, 1701, 1987.

Wittchen, T. et al, Solar cell calibration and characterization: simplified DSR apparatus; Photovoltaic Specialists Conference, Conference Record of the Twentieth IEEE1988, vol. 2, 1988 pp. 1251-1257.

International Search Report in related PCT application WO 2010/135453, Feb. 17, 2011.

Written Opinion of the International Searching Authority in related PCT application WO 2010/135453, Dec. 21, 2010.

* cited by examiner

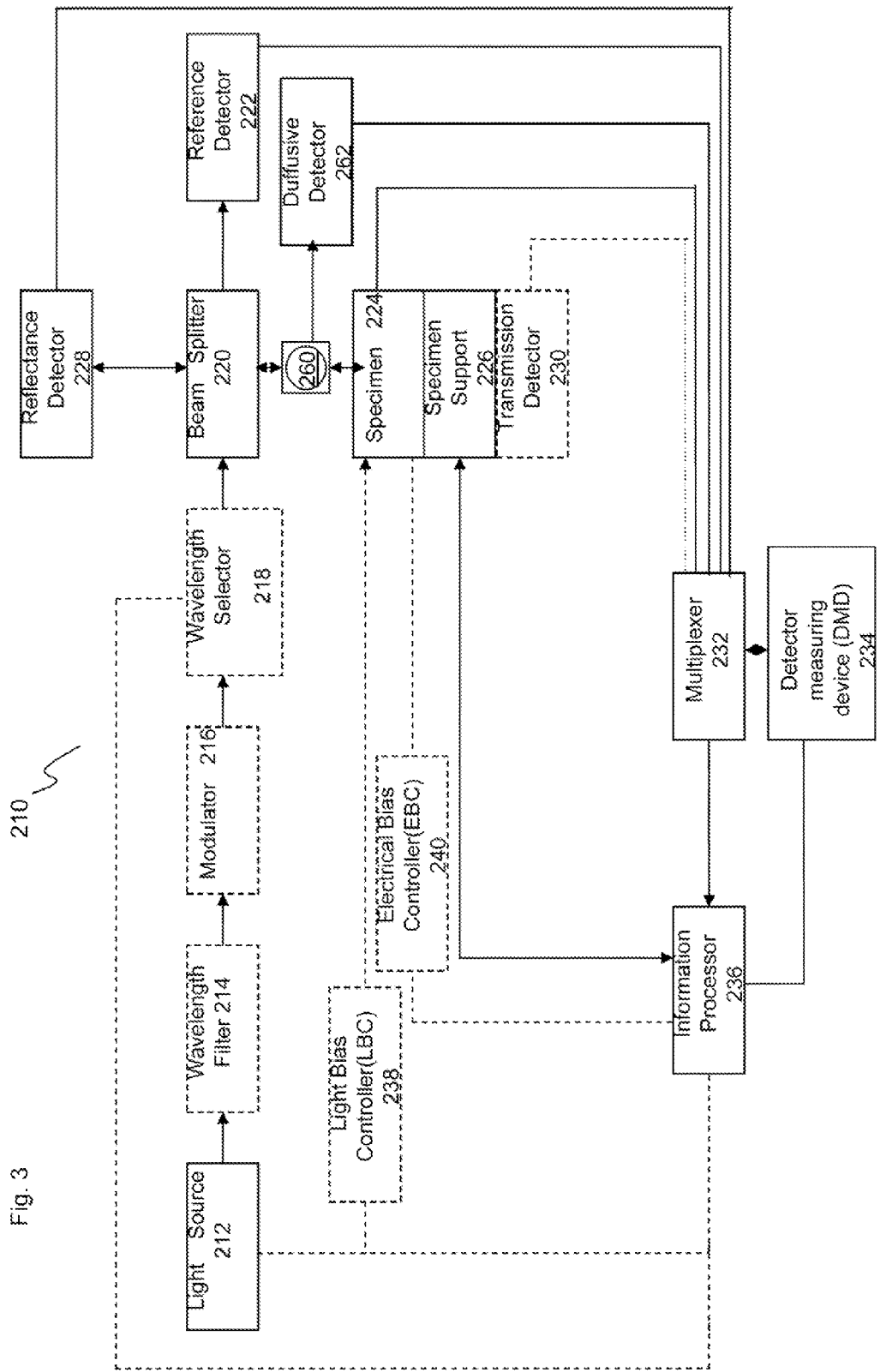

QUANTUM EFFICIENCY MEASUREMENT SYSTEM AND METHOD OF USE

CROSS-REFERENCE TO RELATED APPLICATIONS

This application is a continuation of Patent Cooperation Treaty (PCT) Application PCT/US 10/35445 filed May 19, 2010, entitled "Quantum Efficiency Measurement System and Method of Use", which in turn claims priority to U.S. Provisional Patent Application Ser. No. 61/216,704, filed May 19, 2009. The entire contents of both applications are hereby incorporated by reference.

BACKGROUND

Presently, there are considerable efforts underway to develop sustainable sources of energy. Research into wind-powered generators, wave-powered energy systems, and biofuels has increased dramatically in the last few years. Solar energy has always been seen as one possible source of environmentally-friendly energy. As such, research and development of higher efficiency solar cells has increased recently.

Most silicon-based solar cells utilize a portion of the wavelength spectrum of an incident optical signal to generate photo current. Single junction solar cells produce electricity when illuminated with light within specific, narrow wavelength range. In an effort to increase the efficiency, multiple junction solar devices have been developed. Unlike single junction devices, multi-junction devices feature multiple layers or junctions of photovoltaic/photoactive material. Each layer is configured to generate an electrical charge when irradiated with optical radiation within a specific wavelength range. Typically, the various layers are photoactive in different wavelength ranges, thereby providing a higher efficiency device than single junction solar devices.

Generally, it is desirable to characterize the spectral performance of a solar cell, during the research, development and fabrication phases of the solar device. The parameters currently used to characterize the spectral behavior of a photovoltaic device (PVD) are external quantum efficiency (QE) and internal quantum efficiency (IQE). To that end, PVD I-V curves are commonly used to characterize the global behavior of PVDs. From these curves the following parameters are obtained: $I_{sc}$ (short circuit current), $V_{oc}$ (open circuit voltage), maximum power, solar cell efficiency, and parasitic resistances. Presently there are several methods used to determine the QE of a solar device, such as the dual beam splitter method, integrating sphere method, and the fiber optic-based approaches. While each of the approaches has proven somewhat successful in the past, a number of shortcomings have been identified. For example, both the dual beam splitter method and integrating sphere method require either the sample under examination to be moved from one test station to another or one or more components within the test station need to be removed or replaced with different components in order to obtain reflectance measurements required for the measurement of internal quantum efficiency. As such, characterization of PVDs using these techniques tends to be a time consuming process. In contrast, the fiber optic-based approach offers a flexible testing platform without requiring the additional steps associated with the dual beam splitter approach and integrating sphere approach. Unfortunately, losses associated with light propagation through the fiber introduce uncertainties which could adversely affect the precision in the determination of the internal quantum efficiency.

Thus, in light of the foregoing, there is an ongoing need for improved quantum efficiency measuring systems capable of quickly and accurately measuring the quantum efficiency of samples under examination.

SUMMARY

The present application discloses various systems capable of measuring one or more optical characteristics of a specimen and calculating the quantum efficiency and internal quantum efficiency of the specimen based on the aforementioned optical characteristics. Unlike prior art systems, the present measuring systems do not require additions to or modifications of the various optical components of measuring systems to complete the measuring process. Further, the present systems do not require the specimens under investigation to be repositioned or moved to another measuring station to complete the measuring process. In contrast to prior art systems, the present systems include a multiplexer device capable of simultaneously receiving signals from various detectors and other devices within the measuring system. As such, the present systems have proven capable of efficiently and accurately measuring various optical characteristics of a specimen and accurately calculating the quantum efficiency and internal quantum efficiency of the specimen under review.

In one embodiment, the present application is directed to a system for measuring a characteristic of a solar cell and includes at least one light source irradiating at least one optical signal having a spectral range from about 100 nm to about 3000 nm, at least one wavelength selector configured to selectively narrow the spectral range of the optical signal, at least one beam splitter, at least one reference detector in optical communication with the beam splitter and configured to measure at least one characteristic of the optical signal, at least one specimen irradiated with the optical signal from the beam splitter, at least one reflectance detector in optical communication with the specimen via the beam splitter, the reflectance detector configured to measure at least one optical characteristic of the optical signal reflected by the specimen, at least one multiplexer in communication with at least one of the reference detector, specimen, and reflectance detector, and at least one processor in communication with at least one of the reference detector, specimen, and reflectance detector via the multiplexer, the processor configured to calculate at least one characteristic of the specimen based on data received from at least one of the reference detector, specimen, and reflectance detector.

In another embodiment, the present application is directed to a system for measuring a characteristic of a solar cell and includes at least one light source irradiating at least one optical signal having a spectral range from about 100 nm to about 3000 nm, at least one wavelength selector configured to selectively narrow the spectral range of the optical signal, at least one beam splitter, at least one reference detector in optical communication with the beam splitter and configured to measure at least one characteristic of the optical signal, at least one specimen irradiated with the optical signal from the beam splitter, at least one diffusive device in optical communication with the beam splitter and the specimen, at least one diffusive detector in communication with the diffusive device and configured to measure at least one optical characteristic of light scattered by the specimen when irradiated with the optical signal, at least one reflectance detector in optical communication with the specimen via the diffusive device and the beam splitter, the reflectance detector configured to measure at least one optical characteristic of the optical signal reflected by the specimen, at least one multiplexer in communication with at least one of the reference detector, specimen, the diffusive device, the diffusive detector, and reflectance detector and at least one processor in communication with at least one of the reference detector, specimen, the diffusive device, the diffusive detector, and reflectance detector via the multiplexer, the processor configured to calculate at least one characteristic of the specimen based on data received from at least one of the reference detector, specimen, the diffusive device, the diffusive detector, and reflectance detector.

In another embodiment, the present application discloses various methods of calculating the quantum efficiency and internal quantum efficiency of a specimen. In one embodiment, the present application is directed to a method of measuring the quantum efficiency and internal quantum efficiency of a solar cell and includes generating at least one optical signal having a controlled wavelength and intensity, splitting the optical signal into a first signal and second signal, directing the first signal into a reference detector configured to measure at least one optical characteristic of the first signal, measuring the optical characteristic of the first signal with the reference detector, directing the second signal to a specimen, measuring at least one optical characteristic of the second signal reflected by the specimen with a reflectance detector, measuring a photo-generated electrical signal by specimen at each wavelength of the incident second signal, multiplexing the data from reference and reflectance detectors with a multiplexer simultaneously in communication with the reference and reflectance detectors, and calculating the quantum efficiency of the specimen based on the optical characteristics measured by the reference and reflectance detectors with a processor in communication with a multiplexer.

Other features and advantages of the embodiments of the various quantum efficiency measuring systems as disclosed herein will become apparent from a consideration of the following detailed description.

BRIEF DESCRIPTION OF THE DRAWINGS

Various embodiments of a quantum efficiency measuring system will be explained in more detail by way of the accompanying drawings, wherein:

FIG. 3 shows a schematic diagram of an embodiment of a quantum efficiency measuring system capable of measuring diffused light scattered by the specimen under examination.

DETAILED DESCRIPTION

Figure 1:
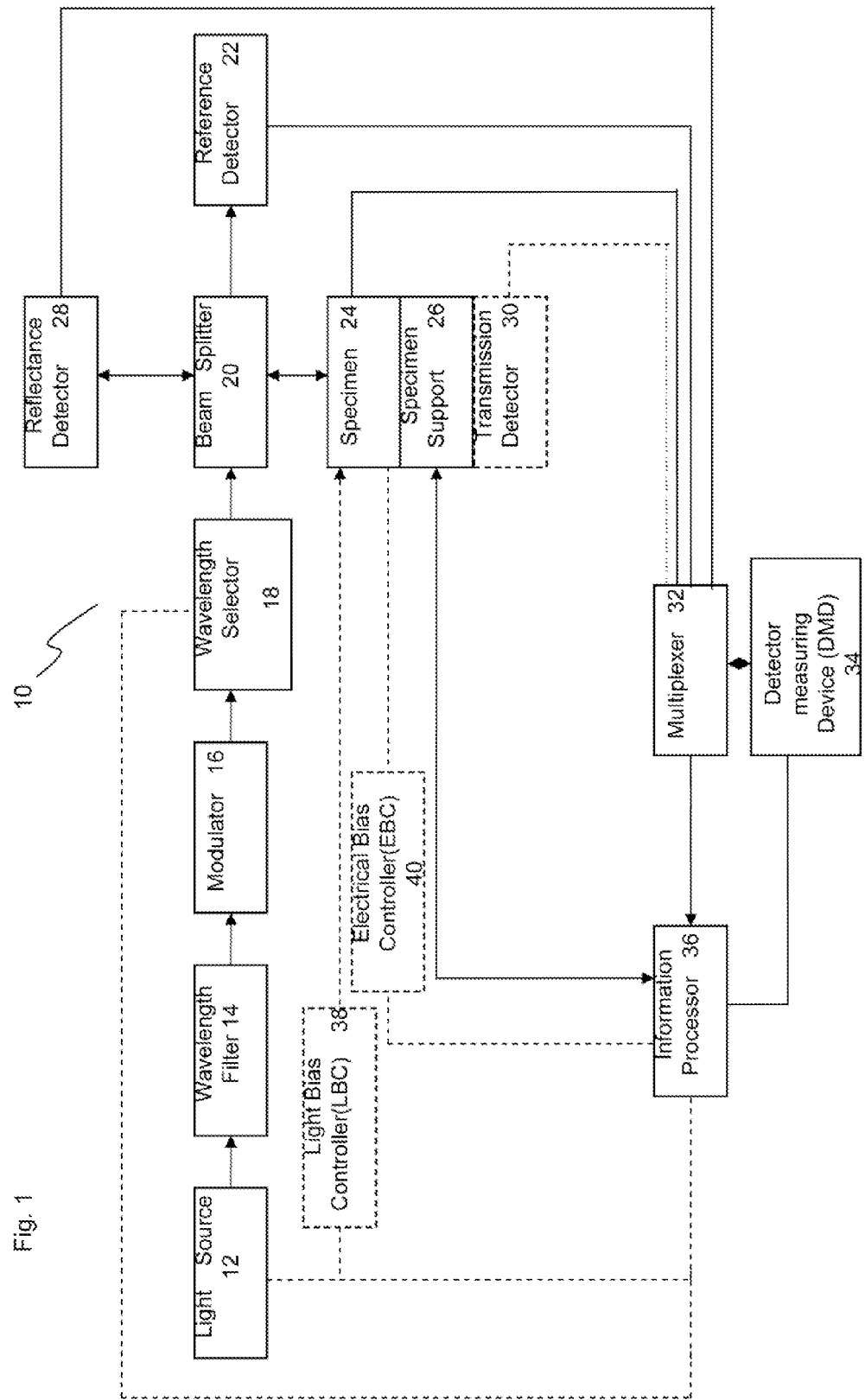
FIG. 1 shows a schematic diagram of an embodiment of a quantum efficiency measuring system configured for measuring a modulated optical signal.

FIG. 1 shows an embodiment of a quantum efficiency measuring system. As shown, the measuring system 10 includes one or more light sources 12 configured to irradiate one or more optical signals to at least one wavelength filter 14. In one embodiment, the light source 12 comprises a quartz tungsten halogen lamp configured to irradiate a broad spectrum optical signal (i.e. from about 300 nm to about 3000 nm) to the wavelength filter 14. Optionally, any variety of alternate light sources 12 could be used with the present system, including, without limitation, arc lamps, xenon lamps, deuterium lamps, and the like. As stated above, the light source 12 may be configured to irradiate a broad spectrum optical signal to the wavelength filter 14. Optionally, the light source 12 may be configured to irradiate a narrow optical signal.

Referring again to FIG. 1, the wavelength filter 14 may comprise any variety of wavelength filter devices. For example, in one embodiment, the wavelength filter 14 comprises an optical filter wheel. As such, the wavelength filter 14 may be configured to receive the broad wavelength spectrum output from the light source 12 and reduce the wavelength range of the optical signal in order to increase the efficiency of wavelength selector 18. Optionally, the wavelength filter 14 may be incorporated into the light source 12. In an alternate embodiment, the wavelength filter 14 need not be included within the measuring system 10.

As shown in FIG. 1, the wavelength filter 14 is in optical communication with one or more modulators 16. The modulator 16 may be configured to partition the continuous optical signal output by the light source 12 into a series of discrete optical signals. In one embodiment, the modulator 16 comprises a light chopper such as the single or dual aperture chopper wheel. In one embodiment, the modulator 16 is configured to produce an optical signal having a frequency of about 8 Hz to about 1100 Hz, although those skilled in the art will appreciate that the light modulator 16 may be configured to produce a modulated signal at any desired frequency. Optionally, like the wavelength filter 14, the modulator 16 may be incorporated into the light source 12. Optionally, the measuring system 10 may be operated without the modulator 16.

Referring again to FIG. 1, one or more wavelength selectors 18 may be included within the measuring device 10 in optical communication with the light source 12. In one embodiment, the wavelength controller 18 comprises a monochromator configured to transmit a mechanically selectable narrow band of wavelengths from the light source 12. For example, in one embodiment, the wavelength selector 18 has a spectral resolution of about 100 nm. In another embodiment, the wavelength selector 18 has a spectral resolution of about 10 nm. Optionally, the wavelength selector 18 may have a spectral resolution of about 0.3 nm. Further, any variety of wavelength selecting devices may be used as a wavelength selector 18, including, without limitations, gratings, grisms, prisms, holographic optical elements, and the like. In one embodiment, the wavelength selector 18 is manually operable. In an alternate embodiment, the wavelength selector 18 may be coupled to a computer, processor, or other controller 36 configured to permit automated adjustment of the wavelength selector 18. Those skilled in the art will appreciate that the wavelength filter 14 and wavelength selector 18 may be combined into a single unit configured to narrow the spectral range of an incident signal to a desired spectral range. For example, the components 12, 14, 16 and 18 shown in FIG. 1 may comprise a tunable modulated optical source. Optionally discrete or tunable lasers could be also used to replace components 12, 14, 16 and 18. As such, the wavelength range, spectral bandwidth and wavelength increment of tunable optical source would preferably be consistent with expected responsivity characteristics of PVD under test.

As shown in FIG. 1, at least one beam splitter or optical signal splitting device 20 is in optical communication with the wavelength selector 18. In one embodiment, the beam splitter 20 comprises a three-way neutral glass substrate having one or more optical coatings applied thereto. Those skilled in the art will appreciate that any variety of optical coatings may be used to manufacture a glass-based beam splitter. In another embodiment, the beam splitter 20 comprises a holographic optical element. Those skilled in the art will appreciate that the beam splitter 20 may comprise any variety of devices, including, without limitations, polymer substrates having one or more coatings applied thereto, silica-based substrates having one or more coatings applied thereto, coated or uncoated metallic substrates, and the like. Further, in one embodiment, the beam splitter 20 is configured to transmit 50% of the optical signal therethrough and reflect 50% of the signal. Optionally, the beam splitter may be configured to transmit between 1% and 99% of the optical signal there through.

Referring again to FIG. 1, the beam splitter 20 transmits at least a portion of the incident optical signal to at least one reference detector 22 and reflects at least a portion of the optical signal to at least one specimen 24 positioned on or otherwise secured by a specimen support 26. In one embodiment the reference detector 22 comprises a photodiode with known spectral characteristics. Optionally, any variety of detectors with known spectral response could be used as a reference detector 22, including, without limitation, photomultipliers, CCD devices, pyrodetectors, and the like.

In one embodiment, the specimen 24 comprises one or more photovoltaic substrates or solar cells. For example, in one embodiment, the specimen 24 comprises one or more monocrystalline silicon wafers. Optionally, the specimen 24 may comprise any variety of photo-active devices or substrates. In another embodiment, any variety of specimens 24 could be supported by the specimen support 26. Further, the specimen 24 may comprise a coated substrate. As such, the measuring system 10 may be used to measure the absorbance of a coated substrate. Alternatively the system from FIG. 1 can be used for the spectral calibration of photosensitive devices. Further, the system can be used to determine reflectance, transmittance, and/or quantum yield for fluorescent components. Further, the specimen support 26 may comprise an optical mount or table configured to securely support the specimen 24. In one embodiment, the specimen support 26 comprises manually adjustable optical mount. In an alternate embodiment, the specimen support 26 may comprise a motorized mount in communication with a controller. Those skilled in the art will appreciate that any variety of mounts or linear stages may be used as a specimen support 26. Further, the specimen support 26 may be configured to maintain the specimen 24 within a desired temperature range. For example, in one embodiment, the specimen support 26 is configured to maintain the specimen 24 within a temperature range of about 10 degrees Celsius. Optionally, the specimen support 26 may be configured to maintain the specimen 24 within a temperature range of about 0.1 degree Celsius.

Referring again to FIG. 1, at least one reflectance detector 28 is positioned to receive light reflected from the specimen 24 and transmitted through the beam splitter 20. In one embodiment, the reflectance detector 28 comprises an optical power meter. In an alternate embodiment, the reflectance detector 28 may comprise a spectral photometer. Optionally, any variety of detectors could be used as a reflectance detector 28, including, without limitation, photomultipliers, CCD devices, power meters, photometers, and the like.

Optionally, one or more transmission detectors 30 may be positioned proximate to the specimen 24 and configured to receive one or more optical signals transmitted there through. Like the reference detector 22 and reflectance detector 28, any variety of detector devices may be used as a transmission detector 30. Optionally, the measuring device 10 may be operated without the transmission detector 30.

As shown in FIG. 1, at least one of the reference detector 22, specimen 24, reflectance detector 28, and transmission detector 30 (if present) may be in communication with at least one multiplexer 32. In one embodiment, the multiplexer 32 comprises a separate piece of equipment. In an alternate embodiment, the multiplexer 32 comprises software that controls the selection of signals coming from different detectors or samples to the detector measuring device (DMD) 34. In one embodiment, the multiplexer 32 is configured to receive one or more signals from the one or more detectors or devices 22, 24, 28, 30 and compare, combine, and/or filter out one or more the received signals, thereby providing a multi-channel measuring system. As such, the multiplexer 32 used herein may permit several detectors or devices 22, 24, 28, 30 to selectively communicate with at least one DMD 34. In one embodiment, the multiplexer 32 is manually operable, thereby permitting the user to select the signals being transmitted to the DMD 34. In an alternate embodiment, the multiplexer 32 may be configured to be controlled by the processor 36 or an alternate control system (not shown), thereby permitting automated signal selection. Optionally, one or more DMD 34 may be coupled to or otherwise in communication with the multiplexer 32. For example, in one embodiment, the DMD 34 comprises at least one lock-in amplifier configured to extract one or more signals having a known carrier wave from an input signal having considerable background noise. In an alternative embodiment the detectors 28, 22, 30 and specimen 24 may include an amplifier to provide the appropriate signal to multiplexer 32 or individual DMD 34. Those skilled in the art will appreciate that any variety of amplifiers can be used with the present system to increase the signal intensity of a desired input signal to the DMD 34. In another embodiment the detectors 28, 22, 30 and specimen 24 can be coupled with individual DMDs 34 controlled by processor 36.

Referring again to FIG. 1, at least one information processor 36 may be used in the present system. As shown, the processor 36 may be in communication with multiple devices used in the measuring system 10. For example, the processor 36 may be in communication with the reference detector 22, specimen 24, reflectance detector 28, and transmission detector 30 (if present) via at least one of the multiplexer 32 and the DMD 34. As such, the processor 36 may be configured to monitor and record data received from at least one of the reference detector 22, specimen 24, reflectance detector 28, and transmission detector 30 (if present). Further, the processor 36 may be in communication with the specimen support 26. For example, the processor 36 may be configured to monitor and regulate the temperature of the specimen support 26 thereby maintaining the specimen 24 supported by the specimen support 26 at a desired temperature. In one embodiment, the processor 36 comprises a personal computer. In an alternate embodiment, the processor 36 may comprise a computer processor board. Optionally, any variety of processing devices may be used with the present system.

Optionally, the measuring system 10 may include various additional devices. For example, as shown in FIG. 1, the measuring system 10 may include at least one light bias controller (LBC) 38. In one embodiment, the light bias controller 38 is configured to permit the variation of the optical signal incident on the specimen 24. For example, the LBC 38 may be in communication with at least one of the light source 12, the processor 36, and the specimen 24. As such, the LBC 38 may receive data from the processor 36 and adjust the output of the light source 12 in response thereto. Optionally, the LBC 38 need not be in communication with the light source 12 or the processor 36. During use, the LBC 38 may be configured to vary the intensity, wavelength range, frequency, power, and/or any other optical characteristic of the optical signal incident on the specimen 24. As such, the LBC 38 may comprise a band-pass filter, spatial filter, light modulator, shutter, grating, optical filter, and the like. Optionally, the measuring system 10 may be operated without a LBC 38. Further, one or more specimen electrical bias controller (EBC) 40 may be in communication with at least one of the specimen 24 and the processor 36. The EBC 40 may be configured to provide multiple functions. For example, the EBC 40 may be configured to provide a bias voltage to the specimen 24. Further, the EBC 40 may be configured to measure an electrical response from the specimen 24 in presence of light. Further, the EBC 40 may be configured to measure the electrical signal generated by the specimen 24 when irradiated with an optical signal from the light source 12. The EBC 40 may also be used to determine I-V curves for specimen 24. Exemplary EBCs 40 may include, without limitations, sourcemeters, programmable electrical sources, and the like. Further, the measuring system 10 may be operated without an EBC 40.

Figure 2:
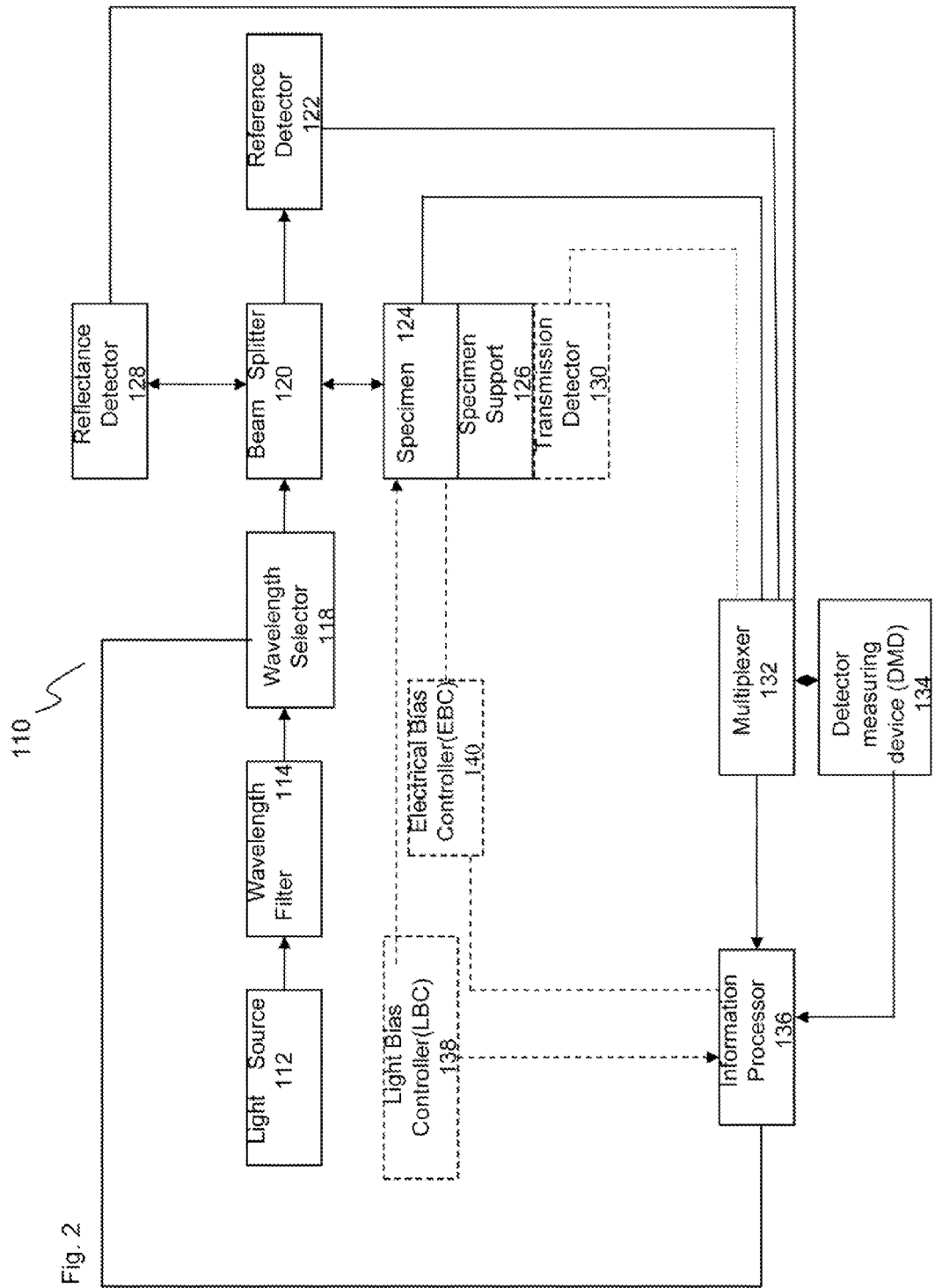
FIG. 2 shows a schematic diagram of an embodiment of a quantum efficiency measuring system configured for measuring a non-modulated optical signal.

FIG. 2 shows an alternate embodiment of a quantum efficiency measuring system. The measuring system 110 shown in FIG. 2 may be used to measure a DC signal, whereas the measuring system shown in FIG. 1 may be configured to measure an AC signal. As shown, the measuring system 110 includes one or more light sources 112 configured to irradiate one or more optical signals to at least one wavelength filter 114. In one embodiment, the light source 112 comprises a quartz tungsten halogen lamp configured to irradiate a broad spectrum optical signal (i.e. from about 300 nm to about 3000 nm) to the wavelength filter 114. Like the previous embodiment, any variety of light sources 112 could be used with the measuring system 110. The light source 112 may be configured to irradiate a broad spectrum optical signal to the wavelength filter 114. Like the previous embodiment, the light source 112 may be configured to irradiate a narrow optical signal.

Referring again to FIG. 2, the wavelength filter 114 may comprise any variety of wavelength filter devices. The wavelength filter 114 may be configured to receive the broad wavelength spectrum output from the light source 112 and reduce the wavelength range of the optical signal in order to increase the efficiency of wavelength selector 118. Optionally, the wavelength filter 114 may be incorporated into the light source 112. In an alternate embodiment, the wavelength filter 114 need not be included within the measuring system 110.

As shown in FIG. 2, the wavelength filter 114 is in optical communication with one or more wavelength controllers 118 included within the measuring device 110. In one embodiment, the wavelength selector 118 comprises a monochromator configured to transmit a mechanically selectable narrow band of wavelengths from the light source 112. Optionally, any variety of wavelength selecting devices may be used as a wavelength selector 118, including, without limitations, gratings, grisms, prisms, holographic optical elements, and the like. In one embodiment, the wavelength selector 18 is manually operable. In an alternate embodiment, the wavelength selector 18 may be coupled to a computer, processor, or other controller configured to permit automated adjustment of the wavelength selector 118.

As shown in FIG. 2, at least one beam splitter or optical signal splitting device 120 is in optical communication with the wavelength selector 118. In one embodiment, the beam splitter 120 comprises a three-way neutral glass substrate having one or more optical coatings applied thereto. Those skilled in the art will appreciate that any variety of optical coatings may be used to manufacture a glass-based beam splitter. Optionally, the beam splitter 120 may comprise a holographic optical element. Those skilled in the art will appreciate that the beam splitter may comprise any variety of devices, including, without limitations, polymer substrates having one or more coatings applied thereto, silica-based substrates having one or more coatings applied thereto, coated or uncoated metallic substrates, and the like. Further, in one embodiment, the beam splitter 120 is configured to transmit 50% of the optical signal there through and reflect 50% of the signal. Optionally, the beam splitter may be configured to transmit between 1% and 99% of the optical signal there through.

Referring again to FIG. 2, the beam splitter 120 transmits at least a portion of the incident optical signal to at least one reference detector 122 and reflects at least a portion of the optical signal to at least one specimen 124 positioned on or otherwise secured by a specimen support 126. In one embodiment the reference detector 22 is a photodiode with known spectral characteristics. Optionally, any variety of detectors with a known spectral response could be used as a reference detector 122, including, without limitation, photomultipliers, CCD devices, pyrodetectors, and the like. Further, the specimen support 126 may comprise an optical mount or table configured to securely support the specimen 124. In one embodiment, the specimen support 126 comprises manually adjustable optical mount. In an alternate embodiment, the specimen support 126 may comprises a motorized mount in communication with a controller. Those skilled in the art will appreciate that any variety of mounts or linear stages may be used as a specimen support 126. Further, the specimen support 126 may be configured to maintain the specimen 124 within a desired temperature range. For example, in one embodiment, the specimen support 126 is configured to maintain the specimen 124 within a temperature range of about 10 degrees Celsius. In one embodiment, the specimen support 126 is configured to maintain the specimen 124 within a temperature range of about 0.1 degree Celsius.

Referring again to FIG. 2, at least one reflectance detector 128 is positioned to receive light reflected from the specimen 124 and transmitted through the beam splitter 120. In one embodiment, the reflectance detector 128 comprises a photodiode with known spectral characteristics. Optionally, any variety of detectors with known spectral response could be used as a reference detector 122, including, without limitation, photomultipliers, CCD devices, pyrodetectors and the like.

Optionally, one or more transmission detectors 130 may be positioned proximate to the specimen 124 and configured to receive one or more optical signals transmitted there through. Like the reference detector 122 and reflectance detector 128, any variety of detector devices may be used as a transmission detector 130. Optionally, the measuring device 110 may be operated without the transmission detector 130.

As shown in FIG. 2, at least one of the reference detector 122, specimen 124, reflectance detector 128, and transmission detector 130 (if present) may be in communication with at least one multiplexer 132. Like the previous embodiment, the multiplexer 132 is configured to receive one or more signals from the one or more detectors or devices 122, 124, 128, 130 and compare, combine, and/or filter out one or more the received signals, thereby providing a multi-channel measuring system. As such, the multiplexer 132 used herein may permit several detectors or devices 122, 124, 128, 130 to selectively communicate with one or more detector measuring devices DMD (134). In one embodiment, the multiplexer 132 is manually operable, thereby permitting the user to select the signals being transmitted to the processor 136. In an alternate embodiment, the multiplexer 132 may be configured to be controlled by the processor 136 or an alternate control system (not shown), thereby permitting automated signal selection. Optionally, one or more DMD 134 may be coupled to or otherwise in communication with the multiplexer 132. For example, in one embodiment, the DMD 134 comprises a DC power meter, such as an optical powermeter. In another embodiment, the DMD 134 comprises an analog-digital converter. In an alternative embodiment each of detectors 128, 122, 130 and specimen 124 may include an amplifier to provide the appropriate signal to multiplexer 132 or individual DMD 134. Those skilled in the art will appreciate that any variety of optional devices 134 coupled be used with the present system, including, without limitations, multimeters, photometers, and the like. In other embodiment, at least one of the detectors 128, 122, 130 and specimen 124 can be coupled with individual DMD controlled by processor 136.

Referring again to FIG. 2, at least one information processor 136 may be used in the present system. As shown, the processor 136 may be in communication with multiple devices used in the measuring system 110. For example, the processor 136 may be in communication with the reference detector 122, specimen 124, reflectance detector 128, and transmission detector 130 (if present) via at least one of the multiplexer 132, and DMD 134. As such, the processor 136 may be configured to monitor and record data received from at least one of the reference detector 122, specimen 124, reflectance detector 128, and transmission detector 130 (if present). Further, the processor 136 may be in communication with the specimen support 126. For example, the processor may be configured to monitor and regulate the temperature of the specimen support 126 thereby maintaining the specimen 124 supported by the specimen support 126 at a desired temperature. In one embodiment, the processor 136 comprises a personal computer. In an alternate embodiment, the processor 136 comprises computer processor board. Optionally, any variety of processing devices may be used with the present system.

Optionally, the measuring system 110 may include various additional devices. For example, like the embodiment shown in FIG. 2, the measuring system 110 may include a light bias controller (LBC) 138. Those skilled in the art will appreciate that the measuring system 110 may be operated without a LBC 138. In one embodiment, the LBC 138 is configured to permit the variation of the optical signal incident on the specimen 124. For example, the LBC 138 may be in communication with at least one of the light source 112, the processor 136, and the specimen 124. As such, the LBC 138 may receive data from the processor 136 and adjust the output of the light source 112 in response thereto. Optionally, the light bias controller 138 may not in communication with the light source 112 or the processor 136. During use, the LBC 138 may be configured to vary the intensity, wavelength range, power, and/or any other optical characteristic of the optical signal incident on the specimen 124. As such, the LBC 138 may comprise a band-pass filter, spatial filter, light modulator, shutter, grating, optical filter, and the like. Further, one or more electrical bias controller (EBC) 140 may be in communication with at least one of the specimen 124 and the processor 136. The EBC 140 may provide multiple functions. For example, the EBC 140 may be configured to provide a bias voltage to the specimen 124 if it is needed. Optionally, the EBC 140 may be configured to measure the electrical response from the specimen 124 in presence of light. The EBC 140 may be configured to measure the electrical signal generated by the specimen 124 when irradiated with an optical signal from the light source 112. Optionally, the EBC 140 can be used to determine I-V curves for specimen 124. Exemplary EBCs 140 include, without limitations, sourcemeters, programmable electrical sources, and the like. Those skilled in the art will appreciate that the measuring system 110 may be operated without a specimen meter 140.

FIG. 3 shows an alternate embodiment of a quantum efficiency measuring system. As shown, the measuring system 210 includes one or more light sources 212 configured to irradiate one or more optical signals. In one embodiment, the light source 212 comprises a quartz tungsten halogen lamp configured to irradiate a broad spectrum optical signal (i.e. from about 300 nm to about 3000 nm). Optionally, any variety of alternate light sources 212 could be used with the present system, including, without limitation, arc lamps, xenon lamps, deuterium lamps, and the like. Like the previous embodiments, the light source 212 may be configured to irradiate a broad spectrum or narrow spectrum optical signal.

Referring again to FIG. 3, at least one wavelength filter 214, at least one modulator 216, and/or at least one wavelength selector 218 may optionally be included in the measuring system 210. Like the previous embodiments, the wavelength filter 214 may comprise any variety of wavelength filter devices. Similarly, any variety of modulators 216 and/or wavelength selectors 218 may be used with the present system 210. Optionally, the wavelength filter 214, modulator 216, and/or the wavelength selector 218 may be incorporated into the light source 212. In an alternate embodiment, the wavelength filter 214, modulator 216, and/or wavelength selector 218 need not be included within the measuring system 210.

As shown in FIG. 3, at least one beam splitter or optical signal splitting device 220 is in optical communication with the light source 212. In one embodiment, the beam splitter 220 comprises a three-way neutral glass substrate having one or more optical coatings applied thereto. Those skilled in the art will appreciate that any variety of optical coatings may be used to manufacture a glass-based beam splitter. In another embodiment, the beam splitter 220 comprises a holographic optical element. Those skilled in the art will appreciate that the beam splitter 220 may comprise any variety of devices, including, without limitations, polymer substrates having one or more coatings applied thereto, silica-based substrates having one or more coatings applied thereto, coated or uncoated metallic substrates, and the like. Further, in one embodiment, the beam splitter 220 is configured to transmit 50% of the optical signal therethrough and reflect 50% of the signal. Optionally, the beam splitter may be configured to transmit between 1% and 99% of the optical signal there through.

Referring again to FIG. 3, like the previous embodiments, the beam splitter 220 transmits at least a portion of the incident optical signal to at least one reference detector 222 and reflects at least a portion of the optical signal through a diffusive device 260 to at least one specimen 224 positioned on or otherwise secured by a specimen support 226. In one embodiment the reference detector 222 comprises a photodiode with known spectral characteristics. Optionally, any variety of detectors with known spectral response could be used as a reference detector 222, including, without limitation, photomultipliers, CCD devices, pyrodetectors, and the like.

As shown in FIG. 3, a diffusive device 260 is positioned between the beam splitter 220 and the specimen 224. In one embodiment, the diffusive device 260 comprises an integrating sphere. Optionally, any variety of alternate diffusive devices 260 may be used with the measuring system 210. The optical signal may be directed through the diffusive device 260 and may be incident on the specimen 224 supported by the specimen support 226. In one embodiment, the specimen 224 comprises one or more photovoltaic substrates or solar cells. For example, in one embodiment, the specimen 224 comprises one or more monocrystalline silicon wafers. Optionally, the specimen 224 may comprise any variety of photo-active devices or substrates. In another embodiment, any variety of specimens 224 could be supported by the specimen support 226. Further, the specimen 224 may comprise a coated substrate. As such, the measuring system 210 may be used to measure the absorbance of a coated substrate. Like the previous embodiments, the measuring system 210 shown in FIG. 3 can be used for the spectral calibration of photosensitive devices. Optionally, the measuring system 210 can be used to determine reflectance, transmittance, and/or quantum yield for fluorescent components.

Referring again to FIG. 3, the specimen support 226 may comprise an optical mount or table configured to securely support the specimen 224. In one embodiment, the specimen support 226 comprises manually adjustable optical mount. Optionally, the specimen support 226 may comprise a motorized mount in communication with a controller. Those skilled in the art will appreciate that any variety of mounts or linear stages may be used as a specimen support 226. Further, the specimen support 226 may be configured to maintain the specimen 224 within a desired temperature range. For example, in one embodiment, the specimen support 226 may be configured to maintain the specimen 224 within a temperature range of about 10 degrees Celsius. Optionally, the specimen support 226 may be configured to maintain the specimen 224 within a temperature range of about 0.1 degree Celsius. As such, the measuring system 210 may optionally include one or more temperature controllers.

As shown in FIG. 3, at least one reflectance detector 228 and at least one diffusive detector 262 may be included in the measuring system 210. As shown, the diffusive detector 262 may be positioned proximate to the diffusive device 260 and configured to detect light scattered or otherwise diffused by the specimen 224. Further, as shown in FIG. 3, the reflectance detector 228 may be positioned to receive light reflected from the specimen 224 and transmitted through the beam splitter 220. In one embodiment, the reflectance detector 228 and/or the diffusive detector 262 comprises an optical power meter. In an alternate embodiment, the reflectance detector 228 and/or the diffusive detector 262 may comprise a spectral photometer. Optionally, any variety of detectors could be used as a reflectance detector 228 and/or a diffusive detector 262, including, without limitation, photomultipliers, CCD devices, power meters, photometers, and the like.

Optionally, one or more transmission detectors 230 may be positioned proximate to the specimen 224 and configured to receive one or more optical signals transmitted there through. Like the reference detector 222, reflectance detector 228, and/or the diffusive detector 262, any variety of detector devices may be used as a transmission detector 230. Optionally, the measuring device 210 may be operated without the transmission detector 230.

As shown in FIG. 3, at least one of the reference detector 222, specimen 224, reflectance detector 228, diffusive device 260, diffusive detector 262, and transmission detector 230 (if present) may be in communication with at least one multiplexer 232. In one embodiment, the multiplexer 232 comprises a separate piece of equipment. In an alternate embodiment, the multiplexer 232 comprises software that controls the selection of signals coming from different detectors or samples to the detector measuring device (DMD) 234. In one embodiment, the multiplexer 232 is configured to receive one or more signals from the reference detector 222, specimen 224, reflectance detector 228, transmission detector 230, and/or diffusive detector 262 and compare, combine, and/or filter out one or more the received signals, thereby providing a multi-channel measuring system. As such, the multiplexer 232 used herein may permit at least one of the reference detector 222, specimen 224, reflectance detector 228, transmission detector 230, and/or diffusive detector 262 to selectively communicate with at least one DMD 234. In one embodiment, the multiplexer 232 is manually operable, thereby permitting the user to select the signals being transmitted to the DMD 234. In an alternate embodiment, the multiplexer 232 may be configured to be controlled by the processor 236 or an alternate control system (not shown), thereby permitting automated signal selection. Optionally, the DMD 234 may be coupled to or otherwise in communication with the multiplexer 232. For example, in one embodiment, the DMD 234 comprises at least one lock-in amplifier configured to extract one or more signals having a known carrier wave from an input signal having considerable background noise. In an alternative embodiment the reference detector 222, specimen 224, reflectance detector 228, transmission detector 230, diffusive device 260, and/or diffusive detector 262 may include an amplifier to provide the appropriate signal to multiplexer 232 or individual DMD 234. Those skilled in the art will appreciate that any variety of amplifiers can be used with the present system to increase the signal intensity of a desired input signal to the DMD 234. In another embodiment the reference detector 222, specimen 224, reflectance detector 228, transmission detector 230, and/or diffusive detector 262 may be coupled with individual DMDs 234 controlled by one or more processors 236.

Referring again to FIG. 3, at least one information processor 236 may be used in the present system. As shown, the processor 236 may be in communication with multiple devices used in the measuring system 210. For example, the processor 236 may be in communication with the reference detector 222, specimen 224, reflectance detector 228, transmission detector 230, and/or diffusive detector 262 via at least one of the multiplexer 232 and the DMD 234. As such, the processor 236 may be configured to monitor and record data received from at least one of the reference detector 222, specimen 224, reflectance detector 228, transmission detector 230, and/or diffusive detector 262. Further, the processor 236 may be in communication with the specimen support 226. For example, the processor 236 may be configured to monitor and regulate the temperature of the specimen support 226 thereby maintaining the specimen 224 supported by the specimen support 226 at a desired temperature. In one embodiment, the processor 236 comprises a personal computer. In an alternate embodiment, the processor 236 may comprise a computer processor board. Optionally, any variety of processing devices may be used with the present system.

Optionally, the measuring system 210 may include various additional devices. Like the previous embodiments, as shown in FIG. 3, the measuring system 210 may include at least one light bias controller (LBC) 238. In one embodiment, the light bias controller 238 is configured to permit the variation of the optical signal incident on the specimen 224. For example, the LBC 238 may be in communication with at least one of the light source 22, the processor 236, and the specimen 224. As such, the LBC 238 may receive data from the processor 236 and adjust the output of the light source 212 in response thereto. Optionally, the LBC 238 need not be in communication with the light source 22 or the processor 236. During use, the LBC 238 may be configured to vary the intensity, wavelength range, frequency, power, and/or any other optical characteristic of the optical signal incident on the specimen 224. As such, the LBC 238 may comprise a band-pass filter, spatial filter, light modulator, shutter, grating, optical filter, and the like. Optionally, the measuring system 210 may be operated without a LBC 238. Further, one or more specimen electrical bias controller (EBC) 240 may be in communication with at least one of the specimen 224 and the processor 236. The EBC 240 may be configured to provide multiple functions. For example, the EBC 240 may be configured to provide a bias voltage to the specimen 224. Further, the EBC 240 may be configured to measure an electrical response from the specimen 224 in presence of light. Further, the EBC 240 may be configured to measure the electrical signal generated by the specimen 224 when irradiated with an optical signal from the light source 212. The EBC 240 may also be used to determine I-V curves for specimen 224. Exemplary EBCs 240 may include, without limitations, sourcemeters, programmable electrical sources, and the like. Further, the measuring system 210 may be operated without an EBC 240.

As shown in FIG. 1, during use the light source 12 irradiates an optical signal having a broad spectral profile. (e.g. from about 100 nm to about 2000 nm) Thereafter, the spectral profile of the optical signal is narrowed by the wavelength filter 14 and the signal is modulated by the modulator 16. Thereafter, the wavelength selector 18 further narrows the wavelength profile of the optical signal. The spectrally narrowed optical signal is then incident on the beam splitter 20 which delivers light simultaneously to the reference detector 22 and the specimen 24. Thereafter, light reflected by the specimen 24 is transmitted through the beam splitter 20 and measured by the reflectance detector 28. Data from the detectors and devices 22, 24, 28, and 30 (if present) may be accessed by the processor 36 via DMD 34 and multiplexer 32. Unlike the prior art systems, the multiplexer 32 enables the measurement from the reference detector 22, specimen 24, reflectance detector 28 and transmission detector 30 (if present) virtually simultaneously without requiring the specimen 24 to be moved to a different testing station or without requiring optical components to be substituted into the measuring system. More specifically, the system shown in FIG. 1 permits a user to simultaneously determine the internal quantum efficiency and external quantum efficiency. For example, the quantum efficiency (QE) may be calculated by the processor using any variety of algorithms or formulas. For example, in one embodiment, the processor 36 may be configured to calculate the quantum efficiency using the following equation:

$$QE(\lambda) = \frac{hc}{q} \frac{R_{pa}(\lambda)}{\lambda}$$

Where h is Plank's constant; c speed of light in vacuum; q is elementary charge and $R_{pa}(\lambda)$ is the power spectral responsivity of sample to be investigated. The power spectral responsivity of sample is determined the signals recorded from sample 24 (in FIG. 1 and reference detector 22, respectively.

Optionally, pre-measurement and responsivity of at least one detector may be performed to determine the responsivity of the reference detector for the calculation of quantum efficiency. Thereafter, the processor 36 may include any number or variety of algorithms or formulas configured to calculate the internal quantum efficiency (IQE). For example, the internal quantum efficiency may be calculate using the following equation:

$$IQE(\lambda) = \frac{QE(\lambda)}{1 - R_{sample}}$$

Where R is the reflectance of sample measured using detector 28 for samples having a strong specular component or using detector 228 and 262 for samples that having a strong diffusive reflectance component.

For sample that have reflectance and transmission components internal quantum efficiency is computed using the following equation:

$$IQE(\lambda) = \frac{QE(\lambda)}{1 - T_{sample} - R_{sample}}$$

Where the transmittance of sample is determined using a detector (e.g. detectors 30, 130 or 230, respectively)

In contrast, as shown in FIG. 3, the light scattered by the specimen 224 during testing would be captured by the diffusive device 260 coupled to the diffusive detector 262. As a result, the system shown in FIG. 3 enables simultaneous measurement from the reference detector 222, specimen 224, reflectance detector 228, transmission detector 230, and/or diffusive detector 262.

In addition to providing the quantum efficiency of a solar cell, the present system may be used to provide IQE scanning images and I-V scanning images or curves of specimens. For example, an IQE scanning image and/or an I-V curve or scanning image may be obtained using the present system. Like the IQE measurement process, the IQE and I-V scanning images may be obtained using the fully automated system shown in FIGS. 1-3. Further, these scanning images may be obtained without requiring the specimen to be repositioned or requiring additional components added to the system.

The foregoing description of the invention is merely illustrative thereof, and it should be understood that variations and modifications can be affected without departing from the scope or spirit of the invention as set forth in the following claims.

What is claimed is:

1. A system for measuring a characteristic of at least one specimen, comprising:
   at least one light source irradiating an at least one optical signal having a spectral range from about 100 nm to about 3000 nm;
   at least one wavelength selector configured to selectively narrow the spectral range of the at least one optical signal;
   at least one beam splitter;
   at least one reference detector in optical communication with the at least one beam splitter and configured to measure at least one characteristic of the at least one optical signal;
   wherein the at least one specimen is irradiated with the at least one optical signal from the at least one beam splitter;
   at least one reflectance detector in optical communication with the at least one specimen via the at least one beam splitter, the at least one reflectance detector configured to measure the at least one optical characteristic of the at least one optical signal reflected by the at least one specimen;
   at least one processor in communication with at least one of the at least one reference detector, the at least one specimen, and the at least one reflectance detector, the at least one processor configured to calculate at least one characteristic of the at least one specimen based on data received from at least one of the at least one reference detector, the at least one specimen, and the at least one reflectance detector, wherein the at least one characteristic of the at least one specimen comprises a quantum efficiency of the at least one specimen.

2. The system of claim 1 further comprising at least one wavelength filter positioned proximate to the at least one light source and configured to spectrally narrow the at least one optical signal irradiated by the at least one light source.

3. The system of claim 1 further comprising at least one modulator positioned proximate to the at least one light source and configured to selectively modulate the at least one optical signal emitted by the at least one light source.

4. The system of claim 1 wherein the at least one processor is configured to calculate the internal quantum efficiency of the at least one specimen based on the calculated quantum efficiency and data received from at least one of the at least one reference detector, the at least one specimen, and the at least one reflectance detector.

5. The system of claim 1 further comprising a transmission detector positioned proximate to the at least one specimen, the transmission detector configured to detect the at least one optical signal irradiated by the at least one light source and transmitted through the at least one specimen.

6. The system of claim 5, further comprising at least one multiplexer, wherein the transmission detector is in communication with the at least one multiplexer.

7. The system of claim 1 further comprising:
at least one multiplexer; and
a detector measuring device in communication with at least one of the at least one multiplexer and the at least one processor.

8. The system of claim 7 wherein the detector measuring device comprises a lock-in amplifier.

9. The system of claim 1 further comprising at least one light bias controller in communication with the at least one processor and the at least one specimen.

10. The system of claim 1 further comprising at least one electrical bias controller in communication with the at least one processor and the at least one specimen.

11. A method of measuring the quantum efficiency and internal quantum efficiency of a specimen, comprising:
generating at least one optical signal having a controlled wavelength and intensity;
splitting the at least one optical signal into a first signal and second signal;
directing the first signal into a reference detector configured to measure at least one optical characteristic of the first signal;
measuring the at least one optical characteristic of the first signal with the reference detector;
directing the second signal to a specimen;
measuring at least one optical characteristic of the second signal reflected by the specimen with a reflectance detector;
measuring a photo-generated electrical signal by the specimen at each wavelength of the incident second signal;
multiplexing the data from reference and reflectance detectors with a multiplexer simultaneously in communication with the reference and reflectance detectors; and
calculating the quantum efficiency of the specimen based on the at least one optical characteristics measured by the reference and reflectance detectors with a processor in communication with a multiplexer.

12. The method of claim 11 further comprising calculating the internal quantum efficiency of the specimen with the processor.

13. The system of claim 1, further comprising at least one multiplexer in communication with at least one of the at least one reference detector, the at least one specimen, and the at least one reflectance detector, wherein the at least one processor is in communication with at least one of the at least one reference detector, the at least one specimen, and the at least one reflectance detector via the at least one multiplexer.

* * * * *